United States Patent
Watkins et al.

(10) Patent No.: US 7,238,210 B2
(45) Date of Patent: Jul. 3, 2007

(54) NON-OXIDATIVE HAIR COLORING USING YOGURT

(75) Inventors: Stephen Watkins, Kent (GB); Heather Eyre, Kent (GB)

(73) Assignee: Quest International Services B.V., Naarden (NL)

(*) Notice: Subject to any disclaimer, the term of this patent is extended or adjusted under 35 U.S.C. 154(b) by 361 days.

(21) Appl. No.: 10/505,144

(22) PCT Filed: Feb. 4, 2003

(86) PCT No.: PCT/GB03/00476

§ 371 (c)(1),
(2), (4) Date: Aug. 20, 2004

(87) PCT Pub. No.: WO03/070208

PCT Pub. Date: Aug. 28, 2003

(65) Prior Publication Data

US 2005/0086744 A1    Apr. 28, 2005

(30) Foreign Application Priority Data

Feb. 22, 2002 (GB) .................................. 0204131.7

(51) Int. Cl.
*A61K 7/13* (2006.01)
(52) U.S. Cl. .................. 8/405; 8/550; 424/70.1; 424/70.14; 132/202; 132/208
(58) Field of Classification Search ............... 424/70.1, 424/70.14; 132/202, 208; 8/405, 550
See application file for complete search history.

(56) References Cited

U.S. PATENT DOCUMENTS 4,268,500 A    5/1981  Cloninger
5,053,219 A *  10/1991 Giddey et al. ................ 424/63

FOREIGN PATENT DOCUMENTS

EP    0 046 326       2/1982
EP    0 518 192 A    12/1992

* cited by examiner

*Primary Examiner*—Eisa Elhilo
(74) *Attorney, Agent, or Firm*—Morgan Lewis & Bockius LLP

(57) ABSTRACT

A non-oxidative hair coloring composition, comprises yogurt or yogurt-derived material. The invention also provides a method of improving the coloring effects of non-oxidative hair coloring compositions, comprising application to the hair (during or after dyeing) of yogurt or a yogurt-derived material. The invention also covers use of yogurt or yogurt-derived material in a hair care composition for the purpose of improving the coloring effects of a non-oxidative hair dye. The invention can be put into effect by incorporating yogurt or yogurt-derived material into a hair care composition for use during non-oxidative dying of hair (i.e. a non-oxidative hair coloring composition) where it acts to improve dye deposition onto hair, or into a composition for use on hair after dyeing by a non-oxidative method, e.g. a shampoo or conditioner composition, to help maintain the color of dyed hair.

11 Claims, No Drawings

NON-OXIDATIVE HAIR COLORING USING YOGURT

FIELD OF THE INVENTION

This concerns hair care compositions, particularly non-oxidative hair colouring compositions, and methods of improving the colour effects including the colour-fastness of non-oxidative hair colouring compositions.

BACKGROUND TO THE INVENTION

Compositions for colouring or dyeing hair can be categorised into temporary, semi-temporary, semi-permanent, permanent and, more recently, the so-called demi-permanent products. Although these names try to describe the general longevity of the colour in terms of wash-out, there is considerable blurring of the categories depending upon the brand of hair colour purchased, the dyes used and the formulation of the carrier base. However, as a guide:
  Temporary lasts only one wash
  Semi-temporary lasts approximately 5 washes
  Semi-permanent lasts approximately 10 washes
  Demi-permanent last approximately 20 washes
  Permanent is not washed out and lasts until the colour fades or grows out Other products on the market are sold as post-colour formulations and these claim to extend the life of the hair colour. These can be split into 'colour maintenance' products, normally shampoos, which are formulated to be mild and help reduce colour washout, and 're-tint' products, which possess a low concentration of colour to reinforce the existing colour of the hair.

The chemistry of hair dyes differs greatly. Temporary and semi-temporary colours tend to be larger molecules that are unable to penetrate the hair shaft and so reside on the hair surface. This makes them easy to remove with washing. Semi-permanent, demi-permanent and permanent colours are smaller molecules, which are able to penetrate the hair shaft, making them more resistant to hair washing.

The following list is a guide to the types of dye often found in the particular category of hair product. It should be noted that many commercially available products contain combinations of dye types:
  Temporary hair colours include food or vegetable dyes or their insoluble lakes (pigments). Here, the colouring formulation normally contains fixatives such as resins to hold the colour onto the hair. These are easily removed with shampoo.
  Semi-temporary dyes are cationic in charge. The cationic charge allows them to bind to the hair surface and makes them more resistant to washing.
  Semi-permanent dyes are normally small, nitro-dyes, which are able to penetrate the hair shaft. This makes them less readily removed with washing.
  Permanent dyes (and couplers) are themselves colourless precursors called oxidation dyes. These precursors, in the presence of peroxide, undergo a chemical reaction to produce coloured compounds of varying degrees of polymerisation. Penetration of the colourless precursors into the hair fibre can be 'encouraged' by the use of an alkali, such as ammonia, which causes the hair shaft to swell and become more porous. Once within the hair fibre, the small colourless precursors polymerize to form the larger coloured compounds. These are then trapped within the hair fibre by their physical size.
  Demi-permanent colours use similar, colourless, precursors to the permanent colours. However, the use of different coupling agents restricts polymerization to the formation of smaller coloured compounds. These smaller compounds are more easily washed out of the hair. Also, the reduction or elimination of ammonia from the formulation helps to limit the penetration of the precursors.

Many products contain a combination of different dye types. For example, some semi-temporary dyes are mixed with the semi-permanent dyes to produce more natural looking shades. The demi-permanent and permanent products can provide a wide variety of colours even on dark hair because the natural hair colour is bleached during the process. The use of the temporary, semi-temporary and semi-permanent colours are dependent upon the individual's natural hair colour; a dark haired person cannot become blond.

The reason for the recent popularity in demi-permanent colouration comes from the desire to produce a more natural look and reduce damage to the hair. Demi-permanent colouring is also used to boost an old, fading, permanent colour.

Semi-temporary or semi-permanent products are used to tint the hair. A growing market for these colours is also in masking gray hair. This is because these types of colours effect the lighter (white) hairs more than the darker hairs, helping to provide a more natural look. However, as described above, such products do not last very long.

SUMMARY OF THE INVENTION

It has surprisingly been found that yogurt or yogurt-derived material has the effect of enhancing the colouring effects of non-oxidative dyes and also enhancing the colour-fastness of hair dyed or coloured by non-oxidative methods.

In one aspect the present invention provides a non-oxidative hair colouring composition, comprising yogurt or yogurt-derived material.

In a further aspect the invention provides a method of improving the colouring effects of non-oxidative hair colouring compositions, comprising application to the hair (during or after dyeing) of yogurt or a yogurt-derived material.

The invention also includes within its scope use of yogurt or yogurt-derived material in a hair care composition for the purpose of improving the colouring effects of a non-oxidative hair dye.

The invention can thus be put into effect by incorporating yogurt or yogurt-derived material into a hair care composition for use during non-oxidative dyeing of hair (i.e. a non-oxidative hair colouring composition) where it acts to improve dye deposition onto hair or into a composition for use on hair after dyeing by a non-oxidative method, e.g. a shampoo or conditioner composition, to help maintain the colour of dyed hair.

The invention improves the colouring effect of non-oxidative dyes by two effects, namely:
  i) by producing improved deposition of colour onto hair when used at the time of colouring treatment (e.g. by being incorporated into a non-oxidative hair colouring composition); and
  ii) by reduced colour loss on washing of dyed hair (e.g. by being incorporated into a shampoo), resulting in better maintenance of colour, i.e. improving colour fastness. The invention can thus enhance the effectiveness and the effective life of non-oxidative hair colouring compositions.

The invention may use yogurt as such, made from whole milk, semi-skimmed milk or skimmed milk. The invention may alternatively use a range of different yogurt-derived proteinaceous materials. In particular, the invention conveniently uses modified yogurt, preferably modified by treatment to remove at least some of the casein proteins. Such modification has the benefits of producing material that is less allergenic (as allergenic effects are generally due to casein proteins), also removing some of the fat content, and producing material that is less prone to smelling (as rancid "off" smells associated with milk and milk-based products are generally due to casein proteins and/or fat). Yogurt may also be further modified by addition of whey proteins to compensate for removal of casein proteins. Such modifications are suitably performed before the fermentation stage in the conventional process for producing yogurt.

Yogurt or modified yogurt as discussed above is conveniently dried, preferably by a spray drying technique, to produce a powdered or granular yogurt-derived material useful in the invention.

It is particularly preferred to use as the yogurt-derived material a spray dried modified yogurt product known by the Trade Mark YOGURTENE (™) and available from Quest International as a food supplement. YOGURTENE (™) consists of selected milk fractions: whey, whey concentrates (components of the serum phase of milk) and non-fat dry milk (2%), that are fermented with classic yogurt bacteria (*Streptococcus thermophilus* and *Lactobacillus bulgaricus*). Whey is the preferred protein source, because casein proteins are associated with allergenic reactions. Once fermentation is complete, the liquid yogurt is spray dried to produce a free-flowing, slightly hygroscopic, low odour white to off-white powder.

Yogurt or yogurt-derived material is suitably present in a hair care composition in an amount in the range 0.01 to 5% by weight, preferably 0.1 to 3% by weight, and more preferably 0.25 to 1% by weight. Very effective results have been obtained with non-oxidative hair colouring compositions and shampoos containing 0.5% Yogurtene.

The hair care compositions can otherwise be of generally conventional formulation.

The invention will be further described, by way of illustration, in the following Examples.

EXAMPLE 1

Semi-Temporary Hair Colours

Three hair swatches were coloured with the same colorant conditioner (the formula of which is given below). The three swatches were temporarily put together to form a single tress and then wetted with water at 45° C. Seventy grams of colour conditioner was gently massaged into the hair tress for approximately 4 minutes, ensuring that the tress was completely coated. The colour was then left in the hair for 15 minutes before being rinsed with running water, at 45° C., until the water ran clear (circa 3 minutes). Finally the tress was dried with a hair-dryer (with gentle combing).

| Conditioner formula: | % w/w |
|---|---|
| Propylene glycol | 17% |
| Hydroxyethylcellulose[1] | 0.6% |
| Phenonip[2] | 0.9% |
| Water | 51.7% |

| Conditioner formula: | % w/w |
|---|---|
| Arlacel 165[3] | 5% |
| Cetyl stearyl alcohol[4] | 3% |
| C12–15 Alkyl Benzoate[5] | 0.5% |
| Cetearyl Isononanoate[6] | 0.5% |
| Lauryl Lactate[7] | 0.5% |
| Water | 20% |
| Colour blend | 0.2% |
| Citric acid | to pH3 |

The colour blend contains: CI 56059 is Basic Blue 99
CI 12245 is Basic Red 76
Ratio red/blue: 40:60
[1]available as Natrosol 250HHR from Aqualon/Hercules, Inc.
[2]Phenoxyethanol (and) methylparaben (and) ethylparaben (and) propylparaben (and) butylparaben, available from Nipa Labs.
[3]Glyceryl Stearate (and) PEG-100 Stearate, available from Uniqema.
[4]available as Lanette O from Cognis.
[5]available as Finsolv TN from Finetex, Inc.
[6]available as Cetiol SN from Cognis.
[7]available as Crodamol LL from Croda Oleochemicals Limited.

The hair tress was then separated into three swatches. One swatch was kept for colour reference and labelled "initial colour". The remaining two swatches were then washed repeatedly with separate shampoos (formulations shown below). One shampoo contained Yogurtene (test) and the other shampoo contained no Yogurtene (control).

| | % w/w |
|---|---|
| Test Shampoo Formulation | |
| Sodium laureth sulfate (28%)[8] | 35.00 |
| Cocamidopropyl betaine (28%)[9] | 10.00 |
| Cocamide DEA[10] | 2.00 |
| Sodium chloride | 2.10 |
| Yogurtene | 0.50 |
| Water | 50.40 |
| Control Shampoo Formulation | |
| Sodium laureth sulfate (28%)[8] | 35.00 |
| Cocamidopropyl betaine (28%)[9] | 10.00 |
| Cocamide DEA[10] | 2.00 |
| Sodium chloride | 2.10 |
| Water | 50.90 |

[8]available as Texapon NSO/IS from Cognis.
[9]available as Tegobetain F50 from Th Goldschmidt AG.
[10]available as Empilan CDE from Cognis.

The two hair swatches were washed seven times following a precise protocol. The swatches were firstly wetted with water at 45° C. Each swatch was 'coated' in 10 grams of shampoo and then, whilst being supported in one hand, rubbed with the fingers in a way that best reproduces the action of washing the hair in vivo. The hair was rinsed clean with running water at 45° C. before being dried with a hair dryer (with gentle combing).

Using a Minolta Colorimeter, hair swatch colour was measured prior to application of the colour, after the hair had been coloured, and after the final (seventh) wash and dry regime. The freshly coloured swatches and the final washed/dried swatches were also visually compared and ranked (blind) for colour intensity, using an untrained panel of volunteers.

The Minolta Colorimeter measures three aspects of colour:

L is the luminosity (0 black and 100 very bright)

a is a green-red scale (negative is green and positive is red)

b is a blue-yellow scale (negative is blue and positive is yellow)

Colorimeter Measurements

| Hair Swatch Colour Before Colouring: | | | |
|---|---|---|---|
| ① L 78.62 | ② L 79.23 | ③ L 78.60 | mean L 78.82 |
| a +2.71 | a +1.89 | a +2.14 | a +2.25 |
| b +20.79 | b +20.08 | b +20.40 | b +20.42 |
| "Initial Colour" Swatch (not washed): | | | |
| ① L 25.25 | ② L 28.82 | ③ L 30.41 | mean L 28.16 |
| a +12.34 | a +13.31 | a +13.23 | a +12.96 |
| b −0.69 | b −1.45 | b −0.50 | b −0.88 |

Swatches After Seven Washes:

|  | Test swatch | Control swatch |
|---|---|---|
| Measure 1 | L 48.94 | L 51.11 |
|  | a +9.80 | a +9.37 |
|  | b +2.79 | b +2.29 |
| Measure 2 | L 48.04 | L 52.58 |
|  | a +10.64 | a +7.91 |
|  | b +1.47 | b +2.95 |
| Measure 3 | L 49.15 | L 55.98 |
|  | a +10.03 | a +7.53 |
|  | b +2.04 | b 4.07 |
| Mean | L 48.89 | L 53.22 |
|  | a +10.16 | a +8.27 |
|  | b +2.10 | b +3.10 |

The colour difference between the freshly coloured hair and the final washed/dried hair (final hair colour—initial hair colour) can be calculated from the Minolta Colorimeter—measurements. This gives Δ L, Δ a and Δ b for each formulation. It should be noted that a smaller Δ L value represents a darker hair swatch (more hair colour), a more negative Δ a value represents less red (less hair colour), and a more positive Δ b value represents less blue (less hair colour):

|  | Δ L | Δ a | Δ b |
|---|---|---|---|
| Test formulation (with Yogurtene) | +20.72 | −2.80 | +2.98 |
| Control formulation (without Yogurtene) | +25.06 | −4.69 | +3.98 |

Visual Assessment (Ranking)

| After 7 washes | Stronger colour | Less coloured |
|---|---|---|
| Volunteer 1 | Yogurtene | No Yogurtene |
| Volunteer 2 | Yogurtene | No Yogurtene |
| Volunteer 3 | Yogurtene | No Yogurtene |
| Volunteer 4 | Yogurtene | No Yogurtene |
| Volunteer 5 | Yogurtene | No Yogurtene |

Analysis of Data

The Δ L, Δ a and Δ b values show that the best colour retention was obtained with the Yogurtene-containing shampoo.

Visual assessment (ranking) of the colour of the hair swatches confirms that the Yogurtene-containing shampoo provided the best colour retention.

Conclusion

The base shampoo, which was formulated using the actives found in most shampoos on the market, was shown to cause a high loss of hair colour over the seven washes. Incorporation of the Yogurtene into the shampoo base reduced the amount of colour lost.

EXAMPLE 2

Semi-Permanent Hair Colours

Two hair swatches, each 21 cm long and weighing 13 grams, were each coloured with a different colour formulae following a precise protocol. One formula contained Yogurtene (test formula), the other did not (control formula):

|  | % w/w |
|---|---|
| Yogurtene Test Colour Formula | |
| Propylene glycol | 10.00 |
| Natrosol 250HHR | 1.50 |
| Phenonip | 0.50 |
| Water | 83.75 |
| Plantacare 2000 UP[1] | 0.25 |
| Cetyl alcohol | 1.50 |
| Ceteareth-20[2] | 1.50 |
| Yogurtene | 0.50 |
| Colour Base | 10.00 |
| Non-Yogurtene Control Colour Formula | |
| Propylene glycol | 10.00 |
| Natrosol 250HHR | 1.50 |
| Phenonip | 0.50 |
| Water | 84.25 |
| Plantacare 2000 UP[1] | 0.25 |
| Cetyl alcohol | 1.50 |
| Ceteareth-20[2] | 1.50 |
| Colour Base | 10.00 |
| The colour base contains: | |
| Ethoxydiglycol | 5.5% |
| Water | 4.2% |
| 3-Nitro-p-hydroxyethylaminophenol | 0.3% |

[1]Sodium Laureth Sulphate (and) Lauryl Glucoside, available from Cognis.
[2]available as Eumulgin B2 from Cognis.

Preparation of the conditioners was carried out by mixing all the ingredients and heating to 80° C. Once the solution had reached the desired temperature it was mixed under high shear. The solution was then cooled with continuous slow stirring. Finally 5 grams of the colour base was added to 45 grams of each of the base formulations.

The hair swatches were first wetted with water at 45° C. Thirty grams of each colour conditioner formula was applied to a single wetted hair swatch and massaged gently into the hair for 3 minutes using a gloved hand. The colour conditioners were left on the hair for 27 minutes before being rinsed with running water, at 45° C., until the water ran clear (circa 2 minutes). Finally the hair swatches were dried using a 500 watt hair-dryer with gentle combing.

Using a Minolta Colorimeter, hair swatch colour was measured prior to application of the colour and after the hair had been coloured and dried. The coloured swatches were also visually compared and ranked (blind) for colour intensity, using an untrained panel of volunteers.

Colorimeter Measurements

Uncoloured Hair Swatches

| ① L 80.06 | ② L 78.98 | ③ L 79.12 | mean L 79.39 |
|---|---|---|---|
| a +0.59 | a +1.90 | a +2.10 | a +1.53 |
| b +17.74 | b +20.22 | b +20.94 | b +19.63 |

After Colouring

|  | Yogurtene swatch | Non-Yogurtene swatch |
|---|---|---|
| Measure 1 | L 57.22 | L 62.06 |
|  | a +35.11 | a +28.11 |
|  | b +31.81 | b +28.22 |
| Measure 2 | L 55.07 | L 60.33 |
|  | a +37.00 | a +31.70 |
|  | b +33.26 | b +29.65 |
| Measure 3 | L 52.87 | L 56.76 |
|  | a +39.60 | a +35.49 |
|  | b +34.18 | b +32.17 |
| Mean | L 55.05 | L 59.72 |
|  | a +37.24 | a +31.77 |
|  | b +33.08 | b +30.01 |

Visual Assessment

|  | Stronger colour | Less coloured |
|---|---|---|
| Volunteer 1 | Yogurtene | No Yogurtene |
| Volunteer 2 | Yogurtene | No Yogurtene |
| Volunteer 3 | Yogurtene | No Yogurtene |
| Volunteer 4 | Yogurtene | No Yogurtene |
| Volunteer 5 | Yogurtene | No Yogurtene |
| Volunteer 6 | Yogurtene | No Yogurtene |

Analysis of Data & Conclusion

Comparison of the mean 'L', 'a' and 'b' values of the swatches shows that the best colour. deposition was obtained with the Yogurtene containing product. The visual assessment (ranking) of the hair swatches confirmed this result.

The invention claimed is:

1. A non-oxidative hair colouring composition, comprising a non-oxidative hair colouring component and yogurt or yogurt-derived material, said yogurt or yogurt-derived material functioning to enhance the colouring effect obtainable with said non-oxidative hair colouring component wherein said yogurt-derived material comprises whey, whey concentrates or non-fat dry milk fermented with yogurt bacteria.

2. A composition according to claim 1, comprising yogurt or yogurt-derived material in an amount in the range 0.01 to 5% by weight.

3. A composition according claim 1, comprising yogurt or yogurt-derived material in an amount in the range 0.25 to 1% by weight.

4. A composition according to claim 3 wherein the yogurt-derived material is modified yogurt.

5. A composition according to claim 4 wherein the modified yogurt is obtained by removal of at least some casein protein from the yogurt.

6. A method of improving the colouring effects of a non-oxidative hair colouring composition, comprising applying said non-oxidative hair colouring composition to the hair and applying yogurt or a yogurt-derived material to the hair before, during or after application of said non-oxidative hair colouring composition to the hair, said yogurt or yogurt-derived material functioning to improve colouring effects obtained with said composition wherein said yogurt-derived material comprises whey, whey concentrates or non-fat dry milk fermented with yogurt bacteria.

7. The method according to claim 6, wherein the yogurt-derived material is modified yogurt.

8. The method according to claim 7, wherein the modified yogurt is yogurt modified by removal of at least some of the casein proteins.

9. The method according to claim 7, wherein the yogurt or modified yogurt is dried.

10. The method according to claim 9, wherein the yogurt or modified yogurt is spray dried.

11. The method according to claim 10, wherein the spray dried modified yogurt comprises Yogurtene.

* * * * *